(12) United States Patent
Funaki (10) Patent No.: US 11,617,547 B2
(45) Date of Patent: Apr. 4, 2023

(54) MEDICAL IMAGE DIAGNOSTIC SYSTEM AND MEDICAL IMAGE DIAGNOSTIC APPARATUS

(71) Applicant: CANON MEDICAL SYSTEMS CORPORATION, Otawara (JP)

(72) Inventor: Tatsuya Funaki, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 102 days.

(21) Appl. No.: 16/874,753

(22) Filed: May 15, 2020

(65) Prior Publication Data

US 2020/0367838 A1  Nov. 26, 2020

(30) Foreign Application Priority Data

May 22, 2019  (JP) .............................. JP2019-096016

(51) Int. Cl.
*A61B 6/00* (2006.01)
*A61B 6/03* (2006.01)
*G16H 40/63* (2018.01)

(52) U.S. Cl.
CPC ............ *A61B 6/035* (2013.01); *A61B 6/4441* (2013.01); *G16H 40/63* (2018.01)

(58) Field of Classification Search
CPC ..................................................... A61B 6/102
See application file for complete search history.

(56) References Cited

FOREIGN PATENT DOCUMENTS

| JP | 2005-130929 A | 5/2005 |
|---|---|---|
| JP | 2012-205681 A | 10/2012 |
| JP | 2014-151085 A | 8/2014 |
| JP | 2017-113083 A | 6/2017 |

OTHER PUBLICATIONS

Japanese Office Action dated Feb. 7, 2023, in Japanese Patent Application No. 2019-096016, 4 pages.

*Primary Examiner* — Dani Fox
(74) *Attorney, Agent, or Firm* — Oblon, McClelland, Maier & Neustadt, L.L.P.

(57) ABSTRACT

A medical image diagnostic system of an embodiment includes a medical image diagnostic apparatus and processing circuitry. The medical image diagnostic apparatus moves on a floor and performs scanogram imaging or main scan imaging. The processing circuitry is configured to acquire a scan protocol to be executed in the medical image diagnostic apparatus, specify a movement range of the medical image diagnostic apparatus on the basis of the scan protocol, acquire information on an area including at least the movement range, and detect or predict presence or absence of an interfering object in the movement range on the basis of the information.

16 Claims, 10 Drawing Sheets

MEDICAL IMAGE DIAGNOSTIC SYSTEM AND MEDICAL IMAGE DIAGNOSTIC APPARATUS

CROSS-REFERENCE TO RELATED APPLICATION

The present application claims priority based on Japanese Patent Application No. 2019-096016, filed on May 22, 2019, the content of which is incorporated herein by reference.

FIELD

Embodiments of the present invention relate to a medical image diagnostic system and a medical image diagnostic apparatus.

BACKGROUND

A medical image diagnostic apparatus in which a gantry that holds an X-ray tube moves and images an examination subject in an indoor space has been known. In the related art with respect to this medical image diagnostic apparatus, a plurality of cameras are installed in an indoor space in which the medical image diagnostic apparatus is disposed, the position of an interfering object in the indoor space is calculated from captured images, and the frame device is moved such that it does not collide with the interfering object. However, application of the related art to a medical image diagnostic apparatus (e.g., IVR-CT apparatus) combined with other apparatuses has not been sufficiently considered, and particularly, prevention of contact between the medical image diagnostic apparatus and other apparatuses and avoidance of the contact have not been sufficiently considered.

DETAILED DESCRIPTION

Hereinafter, a medical image diagnostic system and a medical image diagnostic apparatus of embodiments will be described with reference to the drawings. The medical image diagnostic apparatus acquires medical images of an examination subject mounted on a bed device and performs processing on the medical images to allow diagnosis to be performed on the examination subject. The medical image diagnostic apparatus is, for example, an interventional radiology (IVR)-CT apparatus in which an X-ray computed tomography (CT) apparatus is combined with an X-ray diagnostic apparatus.

A medical image diagnostic system of an embodiment includes a medical image diagnostic apparatus and processing circuitry. The medical image diagnostic apparatus moves on a floor and performs scanogram imaging or main scan imaging. The processing circuitry is configured to acquire a scan protocol to be executed in the medical image diagnostic apparatus, specify a movement range of the medical image diagnostic apparatus on the basis of the scan protocol, acquire information on an area including at least the movement range, and detect or predict presence or absence of an interfering object in the movement range on the basis of the information.

In the IVR-CT apparatus, CT examination according to the X-ray CT apparatus is used in combination with treatment according to the X-ray diagnostic apparatus. For example, a practitioner such as a doctor (hereinafter referred to as an "operator") identifies a part that requires treatment, such as a constriction, with reference to an X-ray CT image (tomographic image) of an examination subject captured by the X-ray CT apparatus. Then, the operator performs endovascular interventional treatment using a catheter while referring to, for example, an X-ray image (transparent image) of the constriction part captured by the X-ray diagnostic apparatus. Although the medical image diagnostic apparatus will be described as an X-ray CT apparatus below, the present invention is not limited thereto.

Figure 1:
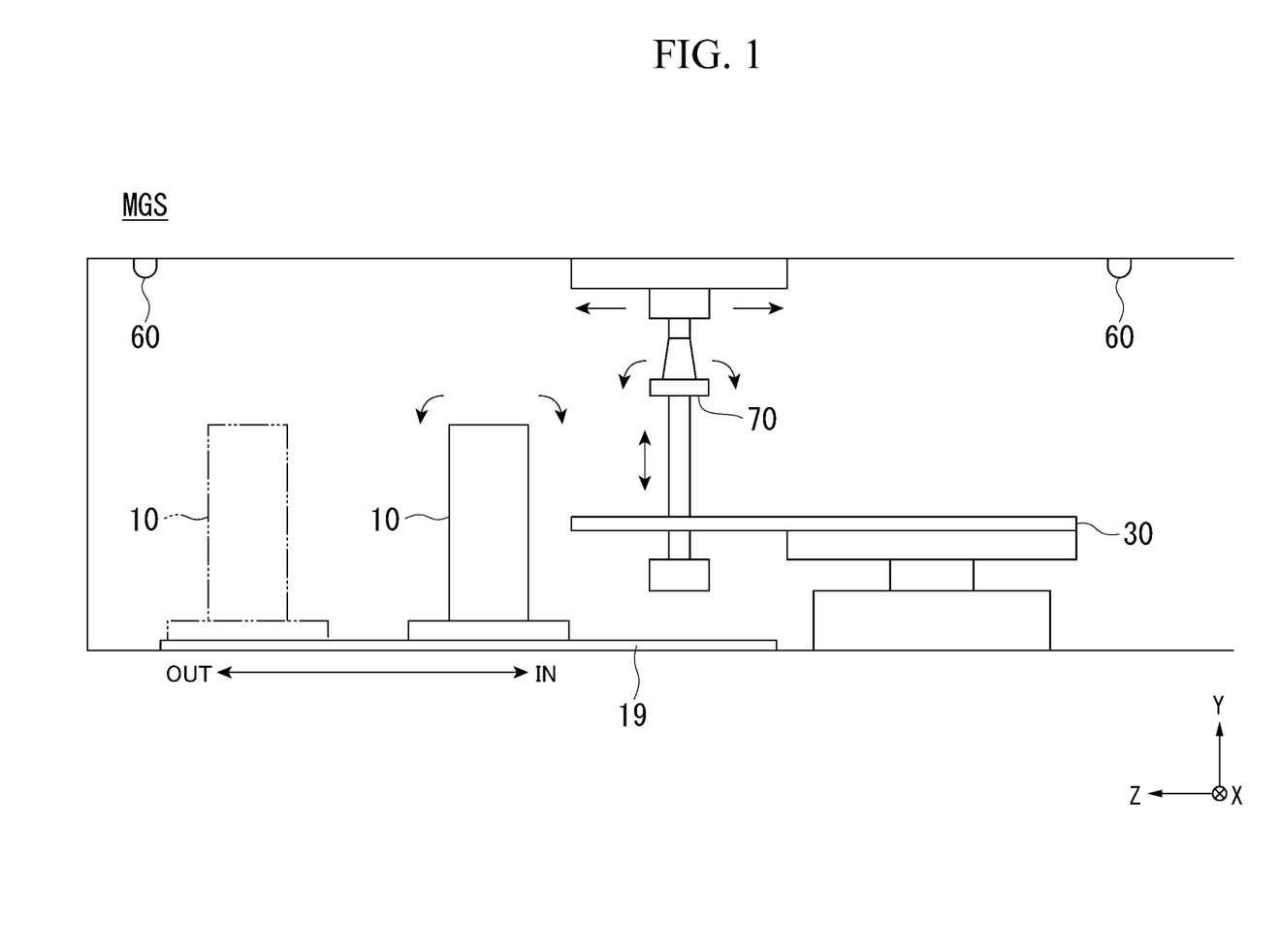
FIG. 1 is a diagram showing an overview of a medical image diagnostic system MGS of an embodiment.

FIG. 1 is a diagram showing an overview of a medical image diagnostic system MGS of an embodiment. The medical image diagnostic system MGS includes, for example, an IVR-CT apparatus 1 and one or more cameras 60. The IVR-CT apparatus 1 includes, for example, a gantry 10, a bed device 30, a console device (not shown), and an IVR device 70. The camera 60 is disposed at a position at which it can recognize the gantry 10, the bed device 30, the TVR device 70, other devices (e.g., portable medical devices, medical carts, and the like), and an operator in real time and detect positions thereof.

The gantry 10 moves along a moving rail 19 provided in a Z-axis direction in the figure and captures an X-ray CT image (tomographic image) of an examination subject mounted on the bed device 30 when imaging of the examination subject is performed. There are cases in which the gantry 10 tilts in a direction Tilt+ or Tilt– according to imaging conditions.

Hereinafter, there are cases in which making the gantry 10 approach nearer to the bed device 30 is referred to as "moving in a direction IN" and separating the gantry 10 from the bed device 30 is referred to as "moving in a direction OUT." For example, the gantry 10 is moved in the direction IN when an X-ray CT image of an examination subject is captured and moved in the direction OUT when imaging ends.

The IVR device 70 is disposed around the bed device 30 and captures an X-ray image (transparent image) of a constriction part of an examination subject mounted on the bed device 30. The IVR device 70 can move in a Y-axis direction in the figure or move in the Z-axis direction in accordance with the constriction part of the examination subject mounted on the bed device 30. In addition, the IVR device 70 can be retracted such that it does not come into contact with the gantry 10 when imaging using the gantry 10 is performed.

The camera 60 images the inside of a room (e.g., operating room) in which the gantry 10 of the IVR-CT apparatus 1 is installed. The camera 60 may be attached to the ceiling of the inside of the room, as shown, or attached to the gantry 10, the IVR device 70, or the like. Installation places of the camera 60 and the number of installed cameras are not particularly limited and may be places and numbers of installed cameras in/with which indoor interfering objects within a range in which the gantry 10 and the TVR device 70 move (e.g., an operator of the IVR-CT apparatus 1 located indoors, peripheral apparatuses, fixtures, and the like placed indoors) can be imaged.

Figure 2:
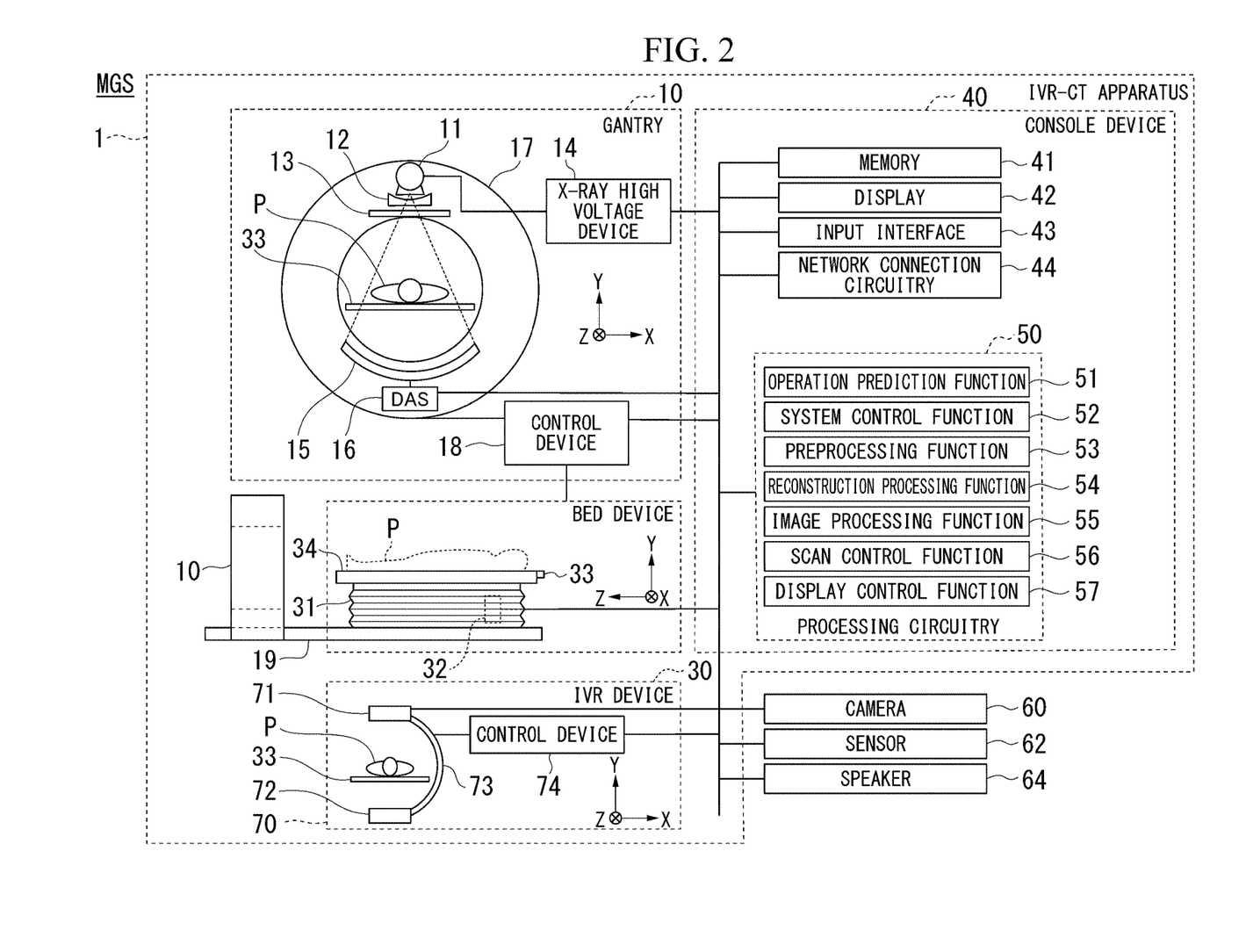
FIG. 2 is a configuration diagram of the medical image diagnostic system MGS including an IVR-CT apparatus 1.

FIG. 2 is a configuration diagram of the medical image diagnostic system MGS including the IVR-CT apparatus 1. The medical image diagnostic system MGS includes, for example, the IVR-CT apparatus 1, the camera 60, a sensor 62, and a speaker 64.

One or more cameras 60 are provided near a ceiling and the like of an installation space of the IVR-CT apparatus 1. It is desirable that the camera 60 is able to derive space information in a height direction (the Y-axis direction of FIG. 2) of an imaging target in such a manner that a plurality of cameras 60 are provided at separate positions, provided at different heights, or the like. The space information in the height direction will be described later.

The sensor 62 is provided in any place on the gantry 10 and detects contact between devices, contact between a device and an examination subject, contact between a device and an operator, contact between a device and fixtures, and the like. The sensor 62 is mainly provided at a place where it is difficult to ascertain contact and interference states of devices from images captured by the camera 60.

The sensor 62 may be provided in the bed device 30, the IVR device 70 or other devices. The sensor 62 may be, for example, a pressure sensor which detects contact with respect to an installed device.

The speaker 64 outputs an alarm sound, a buzzer, and the like in a case where, as a result of processing of the console device 40 which will be described later, likelihood of contact is high. The speaker 64 is an example of an "output."

The IVR-CT apparatus 1 includes, for example, the gantry 10, the bed device 30, the console device 40, and the TVR device 70. Although FTG. 2 shows both a diagram of the gantry 10 viewed in the Z-axis direction and a diagram viewed in the X-axis direction for convenience of description, there is actually one gantry 10. In embodiments, a rotation axis of a rotary frame 17 in a non-tilted state or a longitudinal direction of a top board 33 of the bed device 30 is defined as the Z-axis direction, an axis at a right angle to the Z-axis direction that is parallel to the floor is defined as the X-axis direction, and a direction at a right angle to the Z-axis direction that is perpendicular to the floor is defined as the Y-axis direction.

The gantry 10 includes, for example, an X-ray tube 11, a wedge 12, a collimator 13, an X-ray high voltage device 14, an X-ray detector 15, a data collection system (hereinafter, data acquisition system (DAS)) 16, the rotary frame 17 and a control device 18.

The X-ray tube 11 generates X rays by radiating thermions from a cathode (filament) to an anode (target) according to application of a high voltage from the X-ray high voltage device 14. The X-ray tube 11 includes a vacuum tube. For example, the X-ray tube 11 may be a rotating anode type X-ray tube which generates X rays by radiating thermions to a rotating anode.

The wedge 12 is a filter for controlling the amount of X rays radiated from the X-ray tube 11 to an examination subject P. The wedge 12 attenuates X rays to be transmitted therethrough such that a distribution of the amount of X rays radiated from the X-ray tube 11 to the examination subject P becomes a predetermined distribution. The wedge 12 is also called a wedge filter or a bow-tie filter. For example, the wedge 12 is manufactured by processing aluminum such that it has a predetermined target angle and a predetermined thickness.

The collimator 13 is a mechanism for narrowing a radiation range of X rays that have been transmitted through the wedge 12. The collimator 13 narrows a radiation range of X rays, for example, by forming a slit according to combination of a plurality of lead plates. The collimator 13 may also be called an X-ray aperture.

The X-ray high voltage device 14 includes, for example, a high voltage generation device and an X-ray control device. The high voltage generation device has an electrical circuit including a transformer (trans), a rectifier, and the like and generates a high voltage to be applied to the X-ray tube 11. The X-ray control device controls an output voltage of the high voltage generation device in response to the amount of X rays to be generated by the X-ray tube 11. The high voltage generation device may perform voltage boosting through the aforementioned transformer or perform voltage boosting through an inverter. The X-ray high voltage device 14 may be provided in the rotary frame 17 or provided on the side of a fixed frame (not shown) of the gantry 10.

The X-ray detector 15 detects the intensity of X rays that have been generated by the X-ray tube 11, passed through the examination subject P and applied to the X-ray detector 15. The X-ray detector 15 outputs an electrical signal (an optical signal or the like is also possible) in response to the detected intensity of X rays to the DAS 18. The X-ray detector 15 includes, for example, a plurality of X-ray detection element strings. The plurality of X-ray detection element strings are obtained by arranging a plurality of X-ray detection elements in a channel direction along an arc having the focus of the X-ray tube 11 as a center. The plurality of X-ray detection element strings are arranged in a slice direction (row direction).

The X-ray detector 15 is, for example, an indirect detector including a grid, a scintillator array and an optical sensor array. The scintillator array includes a plurality of scintillators. Each scintillator has scintillator crystals. Scintillator crystals emit an amount of light in response to the intensity of input X rays. The grid is disposed on a surface of the scintillator array to which X rays are input and includes an X-ray shielding plate having a function of absorbing scattered X rays. There is also a case in which the grid is called a collimator (one-dimensional collimator or two-dimensional collimator). The optical sensor array includes, for example, optical sensors such as photomultipliers (PMTs). The optical sensor array outputs an electrical signal in response to the amount of light emitted from the scintillators. The X-ray detector 15 may be a direct conversion type detector including a semiconductor element which converts input X rays into an electrical signal.

The DAS 16 includes, for example, an amplifier, an integrator, and an A/D converter. The amplifier performs amplification processing on an electrical signal output from each X-ray detection element of the X-ray detector 15. The integrator integrates amplified electrical signals over a view period (which will be described later). The A/D converter converts an electrical signal representing an integration result into a digital signal. The DAS 16 outputs detection data based on the digital signal to the console device 40. The detection data is a digital value of an X-ray intensity identified through a channel number and a string number of an X-ray detection element that is a generation source, and a view number indicating a collected view. A view number is a number that varies according to rotation of the rotary frame 17 and is, for example, a number that increases according to rotation of the rotary frame 17. Accordingly, a view number is information representing a rotation angle of the X-ray tube 11. A view period is a period from a rotation angle associated with a certain view number to a rotation angle associated with the next view number. The DAS 16 may detect view switching through a timing signal input from the control device 18, an internal timer, or a signal acquired from a sensor which is not shown. When X rays are continuously emitted by the X-ray tube 11 during full scanning, the DAS 16 collects detection data groups for the entire circumference (360 degrees). When X rays are continuously emitted by the X-ray tube 11 during half scanning, the DAS 16 collects detection data for half a circumference (180 degrees).

The rotary frame 17 is an annular member which supports the X-ray tube 11, the wedge 12, the collimator 13 and the X-ray detector 15 such that the X-ray tube 11, the wedge 12 and the collimator 13 face the X-ray detector 15. The rotary frame 17 is rotatably supported by a fixed frame having the examination subject P introduced thereinto as a center. The rotary frame 17 additionally supports the DAS 16. Detection data output from the DAS 16 is transmitted from a transmitter having a light emitting diode (LED) provided in the rotary frame 17 to a receiver having a photodiode provided in a non-rotary part (e.g., a fixed frame) of the gantry 10 through optical communication and forwarded to the console device 40 through the receiver. A method of transmitting detection data from the rotary frame 17 to a non-rotary part is not limited to the aforementioned method using optical communication and any non-contact type transmission method may be employed. The rotary frame 17 is not limited to an annular member and may be a member such as an arm as long as it can support and rotate the X-ray tube 11 and the like.

Although the IVR-CT apparatus 1 may be, for example, a Rotate/Rotate-Type X-ray CT apparatus (third-generation CT) in which both the X-ray tube 11 and the X-ray detector 15 are supported by the rotary frame 17 and rotate around the examination subject P, it is not limited thereto and may be a Stationary/Rotate-Type X-ray CT apparatus (fourth-generation CT) in which a plurality of X-ray detection elements arranged in an annular shape are fixed to a fixed frame and the X-ray tube 11 rotates around the examination subject P.

The control device 18 includes, for example, processing circuitry having a processor such as a central processing unit (CPU) and a driving mechanism including a motor, an actuator, and the like. The control device 18 receives an input signal from an input interface 43 attached to the console device 40 or the gantry 10 and controls operations of the gantry 10 and the bed device 30.

For example, the control device 18 may rotate the rotary frame 17, tilt the gantry 10 or move the top board 33 of the bed device 30. When the control device 18 tilts the gantry 10, the control device 18 rotates the rotary frame 17 on an axis parallel to the Z-axis direction on the basis of an inclination angle (tilt angle) input to the input interface 43. The control device 18 ascertains a rotation angle of the rotary frame 17 through an output of a sensor which is not shown, and the like. The control device 18 provides the rotation angle of the rotary frame 17 to processing circuitry 50 at any time. The control device 18 may be provided in the gantry 10 or provided in the console device 40.

The control device 18 causes the gantry 10 to move along the moving rail to perform main scan imaging or perform scanogram imaging that is positioning imaging performed before main scan imaging.

The bed device 30 moves the examination subject P to be scanned mounted thereon and introduces the examination subject P into the rotary frame 17 of the gantry 10. The bed device 30 includes, for example, a base 31, a bed driving device 32, the top board 33, and a supporting frame 34. The base 31 includes a housing which supports the supporting frame 34 such that the supporting frame 34 can move in a vertical direction (Y-axis direction). The bed driving device 32 includes a motor and an actuator. The bed driving device 32 moves the top board 33 on which the examination subject P is mounted in the longitudinal direction (Z-axis direction) of the top board 33 along the supporting frame 34. The top board 33 is a plate-shaped member on which the examination subject P is mounted.

The console device 40 includes, for example, a memory 41, a display 42, the input interface 43, a memory 41, a network connection circuit 44, and the processing circuitry 50. Although the console device 40 is described as a body separate from the gantry 10 in embodiments, some or all components of the console device 40 may be included in the gantry 10.

The memory 41 is realized, for example, by a semiconductor element such as a random access memory (RAM) or a flash memory, a hard disk, an optical disc, or the like. The memory 41 stores, for example, detection data, projection data, reconstructed images, CT images, and the like. Such data may be stored in an external memory with which the IVR-CT apparatus 1 can communicate instead of the memory 41 (or in addition to the memory 41). For example, the external memory may be controlled through a cloud server which manages the external memory by receiving a read/write request.

The display 42 displays various types of information. For example, the display 42 displays medical images (CT images) generated by processing circuitry, graphical user interface (GUI) images through which various operations from an operator are received, and the like. For example, the display 42 may be a liquid crystal display, a cathode ray tube (CRT), an organic electroluminescence (EL) display, or the like. The display 42 may be provided in the gantry 10. The display 42 may be a desktop type or a display device (e.g., a tablet terminal) which can wirelessly communicate with the main body of the console device 40. The display 42 is another example of the "output."

The input interface 43 receives various input operations from an operator and outputs electrical signals representing details of received input operations to the processing circuitry 50. For example, the input interface 43 receives operations of inputting collection conditions when detection data or projection data (which will be described later) is collected, reconstruction conditions when a CT image is reconstructed, image processing conditions when a postprocessing image is generated from a CT image, and the like. For example, the input interface 43 is realized by a mouse, a keyboard, a touch panel, a trackball, a switch, a button, a joystick, a foot pedal, a camera, an infrared sensor, a microphone, or the like. The input interface 43 may be provided in the gantry 10. The input interface 43 may be realized by a display device (e.g., a tablet terminal) which can wirelessly communicate with the main body of the console device 40.

The network connection circuit 44 includes, for example, a network card having a printed circuit board, a wireless communication module, or the like. The network connection circuit 44 implements an information communication protocol in accordance with the form of a network to be connected thereto. The network includes, for example, a local area network (LAN), a wide area network (WAN), the Internet, a cellular network, a dedicated line, or the like.

The processing circuitry 50 controls the overall operation of the IVR-CT apparatus 1. The processing circuitry 50 executes, for example, an operation prediction function 51, a system control function 52, a preprocessing function 53, a reconstruction processing function 54, an image processing function 55, a scan control function 56, a display control function 57, and the like. For example, the processing circuitry 50 realizes these functions by a hardware processor executing a program stored in the memory 41.

The hardware processor refers to, for example, a circuit (circuitry) such as a CPU, a graphics processing unit (GPU), an application specific integrated circuit (ASIC), or a programmable logic device (e.g., a simple programmable logic device (SPLD), a complex programmable logic device (CPLD), or a field programmable gate array (FPGA)). The program may be directly incorporated into the circuit of the hardware processor instead of being stored in the memory 41. In this case, the hardware processor realizes functions by reading and executing the program incorporated into the circuit. The hardware processor is not limited to a configuration as a single circuit and may be configured as a single hardware processor by combining a plurality of independent circuits to realize respective functions. Furthermore, a plurality of components may be integrated into a single hardware processor to realize respective functions.

Components included in the console device 40 or the processing circuitry 50 may be distributed and realized by a plurality of hardware circuits. The processing circuitry 50 may be realized by a processing device which can communicate with the console device 40 instead of being included in the console device 40. For example, the processing device may be a workstation connected to a single X-ray CT apparatus or a device (e.g., a cloud server) which is connected to a plurality of X-ray CT apparatuses and integrally executes processes equivalent to those of the processing circuitry 50 which will be described below.

The operation prediction function 51 predicts operations of the gantry 10, the bed device 30, the IVR device 70, other devices, an operator, and the like in the installation space of the IVR-CT apparatus 1. The operation prediction function 51 also predicts a position of the operator. The prediction of the operation prediction function 51 is mainly performed immediately before start of movement of the gantry 10 and during movement of the gantry 10. The operation prediction function 51 will be described in detail later.

The system control function 52 controls various functions of the processing circuitry 50 on the basis of input operations received through the input interface 43.

The preprocessing function 53 performs preprocessing such as logarithmic conversion processing, offset correction processing, inter-channel sensitivity correction processing and beam hardening correction on detection data output from the DAS 16, generates projection data, and stores the generated projection data in the memory 41. Processing of the preprocessing function 53 will be described in detail later.

The reconstruction processing function 54 performs reconstruction processing using a filter correction reverse projection method, a sequential approximation reconstruction method or the like on the projection data generated by the preprocessing function 53 to generate CT image data and stores the generated CT image data in the memory 41. The reconstruction processing function 54 is an example of a "reconstructor."

The image processing function 55 converts a CT image into a three-dimensional image or section image data with an arbitrary section through a known method on the basis of an input operation received by the input interface 43. Conversion into a three-dimensional image may be performed by the preprocessing function 53. The image processing function 55 may analyze an image of section image data and classify a body type of an examination subject on the basis of an analysis result.

The scan control function 56 instructs the X-ray high voltage device 14, the DAS 16, the control device 18, and the bed driving device 32 to control detection data collection processing in the gantry 10. The scan control function 56 controls operation of each component when imaging for collecting scanogram images and capturing of images used for diagnosis are performed.

The display control function 57 controls a display mode of the display 42.

According to the above-described configuration, the IVR-CT apparatus 1 performs main scan imaging of the examination subject P in a mode such as helical scan or step-and-shoot scan. The helical scan is a mode of rotating the rotary frame 17 while moving the top board 33 to scan the examination subject P in a spiral form. The step-and-shot scan is a mode of moving the position of the top board 33 at specific intervals to perform a conventional scan in a plurality of scan areas.

The IVR device 70 includes, for example, an X-ray tube 71, an X-ray detector 72, a C arm 73, and a control device 74.

The X-ray tube 71 has the same function as that of the X-ray tube 11 of the gantry 10. The X-ray tube 71 may further have the functions of the wedge 12 and the collimator 13 of the gantry 10. The X-ray detector 72 has the same functions as those of the X-ray detector 15 and the DAS 16 of the gantry 10. The C arm 73 supports the X-ray tube 71 and the X-ray detector 72 such that they face each other. The pair of the X-ray tube 71 and the X-ray detector 72 is configured such that they rotate around a geometrical rotation center (isocenter).

The control device 74 includes, for example, processing circuitry having a processor such as a central processing unit (CPU) and a driving mechanism including a motor, an actuator, and the like. The control device 74 receives an input signal from the console device 40 or the input interface 43 and controls the operation of the C arm 73. The control device 74 may be included in the control device 18 of the gantry 10.

Figure 3:
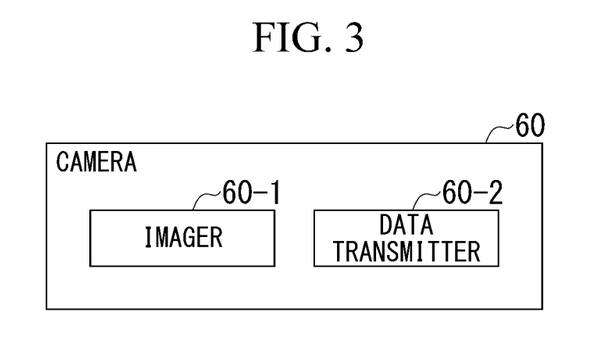
FIG. 3 is a configuration diagram of a camera 60.

FIG. 3 is a configuration diagram of the camera 60. The camera 60 includes, for example, an imager 60-1 and a data transmitter 60-2. The imager 60-1 is a digital camera using a solid-state imaging element such as a charge coupled device (CCD) or a complementary metal oxide semiconductor (CMOS). The imager 60-1 may be an infrared camera. The data transmitter 60-2 communicates with the console device 40 in a wired or wireless manner and transmits an imaging result obtained by the imager 60-1 to the console device 40. The imaging result obtained by the imager 60-1 is stored in the memory 41, for example, and referred to in processing performed by the processing circuitry 50.

Figure 4:
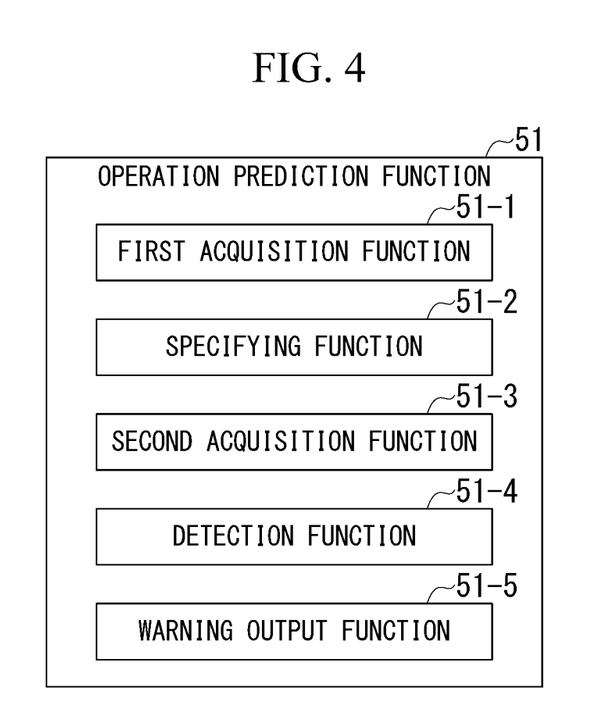
FIG. 4 is a configuration diagram of an operation prediction function 51.

FIG. 4 is a configuration diagram of the operation prediction function 51. The operation prediction function 51 includes, for example, a first acquisition function 51-1, a specifying function 51-2, a second acquisition function 51-3, a detection function 51-4, and a warning output function 51-5.

The first acquisition function 51-1 acquires a scan protocol of X-ray CT imaging performed by the gantry 10 of the IVR-CT apparatus 1. The scan protocol includes information such as imaging conditions of X-ray CT imaging, contrast radiography conditions, and image display methods. The first acquisition function 51-1 is an example of a "first acquirer."

The specifying function 51-2 specifies a movement range of the IVR-CT apparatus 1 on the basis of the scan protocol acquired by the first acquisition function 51-1. The movement range of the 1VR-CT apparatus 1 includes a movement range of the gantry 10 and a movement range of the IVR device 70. The specifying function 51-2 is an example of a "specifier."

The specifying function 51-2 specifies the movement range on the basis of information about a scan range (e.g., the chest of the examination subject P) included in the scan protocol acquired by the first acquisition function 51-1. The scan range included in the scan protocol may be a scan range during scanogram imaging or a scan range during main scan imaging.

The second acquisition function 51-3 acquires information about an area including at least the movement range specified by the specifying function 51-2. The second acquisition function 51-3 acquires, for example, information about a position of the top board 33 of the bed device 30, positions of other devices, and a position of the operator within the area including the movement range by analyzing an image captured by the camera 60. The second acquisition function 51-3 is an example of a "second acquirer."

When space information in a height direction (Y-axis direction in FIG. 2) perpendicular to the horizontal plane on which the gantry 10 is installed, observed in a direction perpendicular to the movement direction of the gantry 10, such as installation of a plurality of cameras 60 at different heights, can be acquired, the second acquisition function 51-3 may acquire an image from which space information in the height direction in the installation space of the IVR-CT apparatus 1, particularly, the gantry 10, can be acquired from an installation space image 41-5.

The detection function 51-4 detects or predicts whether there is an interfering object in the movement range on the basis of the information about the area acquired by the second acquisition function 51-3. Interfering object detection processing and prediction processing executed by the detection function 51-4 will be described in detail later. The detection function 51-4 is an example of a "detector."

The warning output function 51-5 controls output of warning information such that the warning information is output through the display 42 or the speaker 64 when an interfering object has been detected or occurrence of an interfering object has been predicted by the detection function 51-4. The warning output function 51-5 is an example of a "warning output."

When the IVR device 70 has been detected as an interfering object, the detection function 51-4 may output an instruction to the system control function 52 such that the IVR device 70 is moved to a position at which it does not interfere with persons and other devices in the space in a direction in which it becomes further away from a specific area instead of causing the warning output function 51-5 to output warning information.

Figure 5:
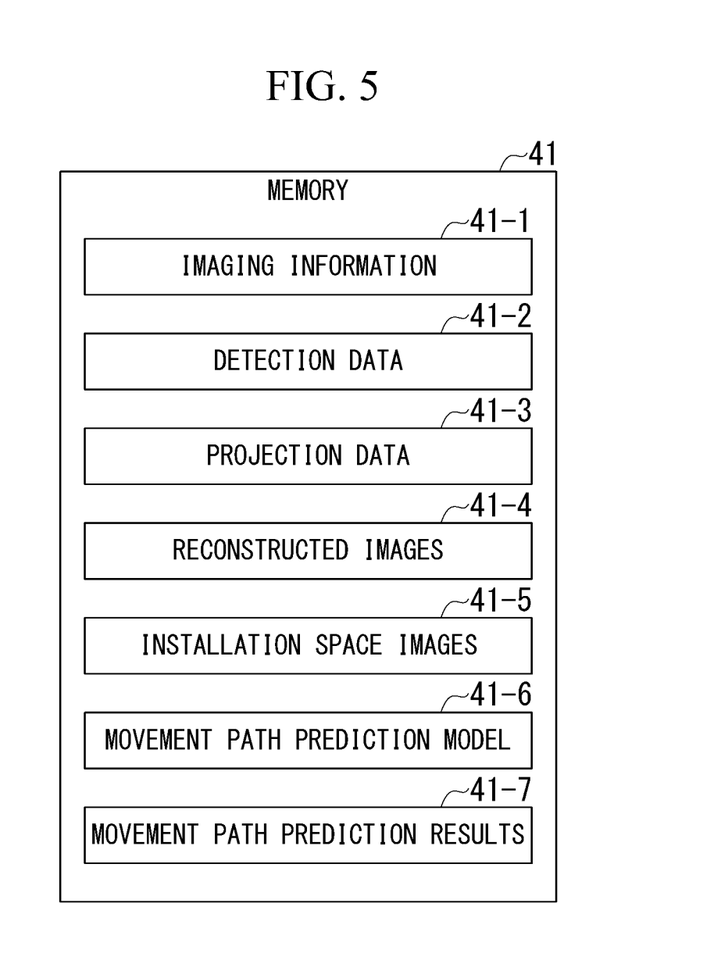
FIG. 5 is a diagram showing an example of data stored in a memory 41.

FIG. 5 is a diagram showing an example of data stored in the memory 41. As shown in FTG. 5, the memory 41 stores, for example, information such as imaging information 41-1, detection data 41-2, projection data 41-3, reconstructed images 41-4, installation space images 41-5, a movement path prediction model 41-6, movement path prediction results 41-7 generated by the processing circuitry 50.

The imaging information 41-1 includes, for example, body information (e.g., the sex, age, height and weight) of the examination subject P, a position of the examination subject P mounted on the top board 33, imaging conditions and contrast radiography conditions of the examination subject P, and the like. The imaging information 41-1 may be input as numerical values, estimates, and the like by the operator of the IVR-CT apparatus 1 through the input interface 43 or may be received from an external device (e.g., an electronic medical records system, or the like). The imaging information 41-1 may include information on the scan protocol acquired by the first acquisition function 51-1.

The reconstructed images 41-4 may include images captured during positioning and images captured during main imaging.

The installation space images 41-5 are images of the indoor space in which the IVR-CT apparatus 1 is installed captured by the camera 60. The installation space images 41-5 include images of the indoor space in a state in which the examination subject P is not mounted on the bed device 30 (a vacant state) and images of the indoor space in a state in which the examination subject P is mounted on the bed device 30.

Figure 6:
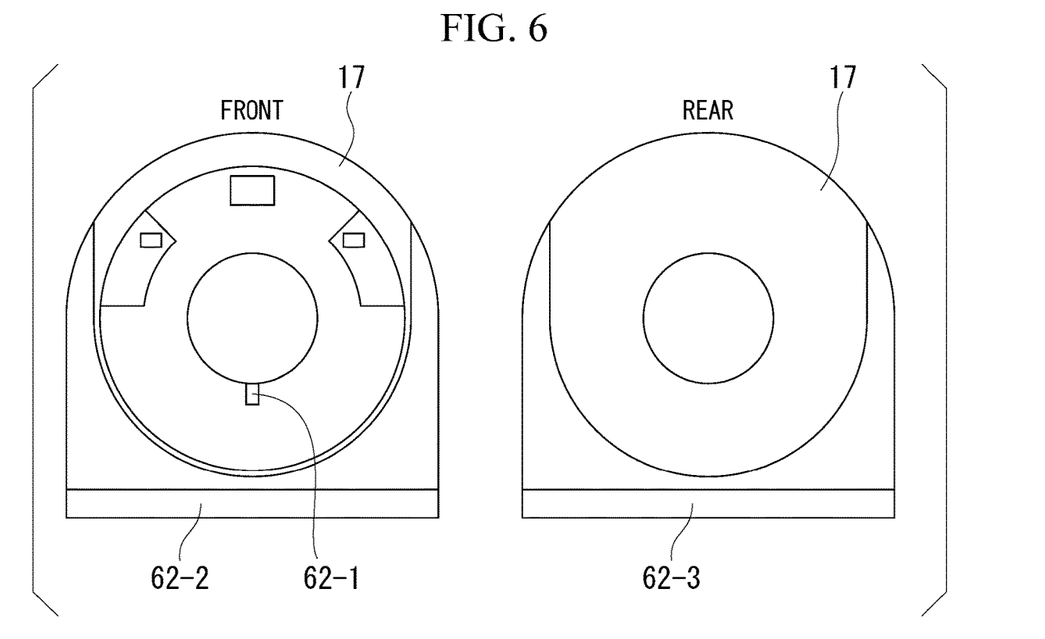
FIG. 6 is a diagram for describing an installation example of a sensor 62.

FIG. 6 is a diagram for describing an installation example of the sensor 62. The sensor 62 is provided, for example, on a side FRONT of the gantry 10 (left of FIG. 6) and a side REAR (right of FIG. 6). The side FRONT is a side of the gantry 10 in proximity to the installation place of the bed device 30 and the side REAR is a side of the gantry 10 separate from the installation place of the bed device 30. The top board 33 on which the examination subject P is mounted is inserted from the side FRONT of the gantry 10.

For example, a tape switch sensor 62-1 and a front MAT switch sensor 62-2 are provided on the side FRONT and a rear MAT switch sensor 62-3 is provided on the side REAR. The tape switch sensor 62-1, the front MAT switch sensor 62-2, and the rear MAT switch 62-3 are contact sensors (pressure sensors). When at least any one of the tape switch sensor 62-1, the front MAT switch sensor 62-2, and the rear MAT switch 62-3 detects contact during movement of the gantry 10, the gantry 10 stops moving and causes the display 42 or the speaker 64 to output warning information.

The operation prediction function 51 predicts a movement path of the gantry 10 and predicts presence or absence of occurrence of an interfering object in order to prevent an interfering object from coining into contact with an area where the sensor 62 cannot detect contact other than the installation place of the sensor 62 shown in FIG. 6.

Figure 7:
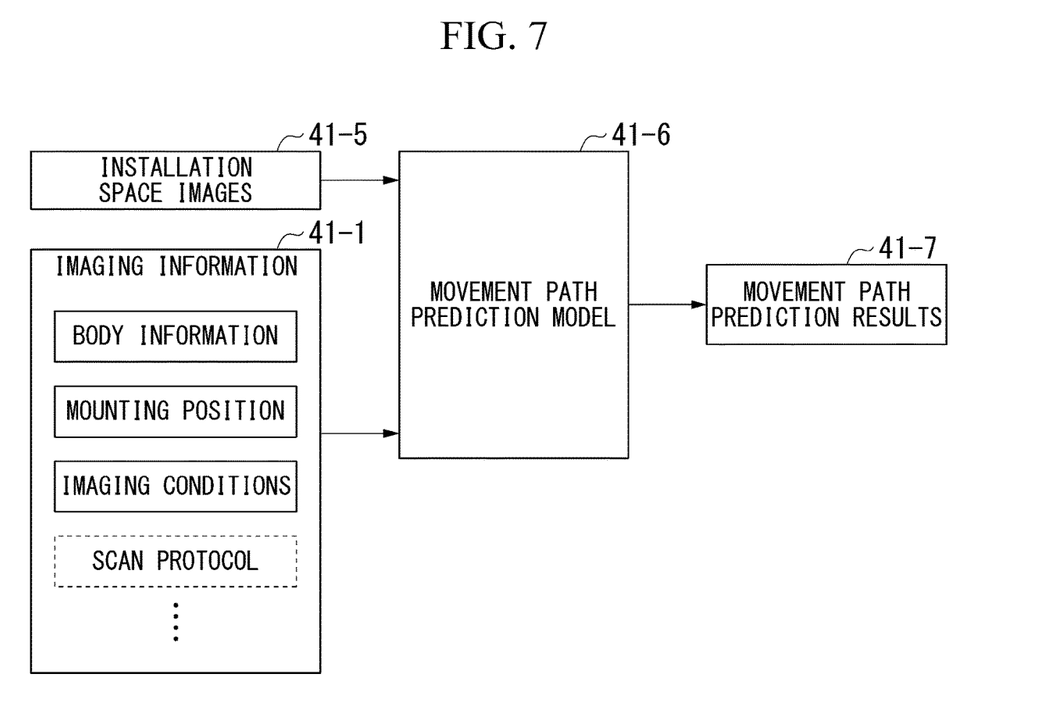
FIG. 7 is a diagram for describing details of interfering object prediction processing performed by the operation prediction function 51.

FIG. 7 is a diagram for describing details of interfering object prediction processing executed by the operation prediction function 51. The movement path prediction model 41-6 is a model which receives some or all information included in the imaging information 41-1 as parameters and is created in advance to reflect space information of the indoor space in which the IVR-CT apparatus 1 is installed and characteristics such as areas where the gantry 10 and the IVR device 70 of the IVR-CT apparatus 1 can move.

The movement path prediction model 41-6 receives some or all imaging information 41-1 and the installation space images 41-5 and predicts a movement path of the gantry 10 in accordance with a scan protocol and presence or absence of contact between an interfering object and the IVR device 70, other devices, an operator, or the like (possibility of contact with an interfering object) during movement of the gantry 10. The movement path prediction model 41-6 stores a calculation result and a result of prediction of presence or absence of contact with an interfering object in the memory 41 as the movement path prediction results 41-7.

[Operation Detection/Prediction Example 1]

Figure 8:
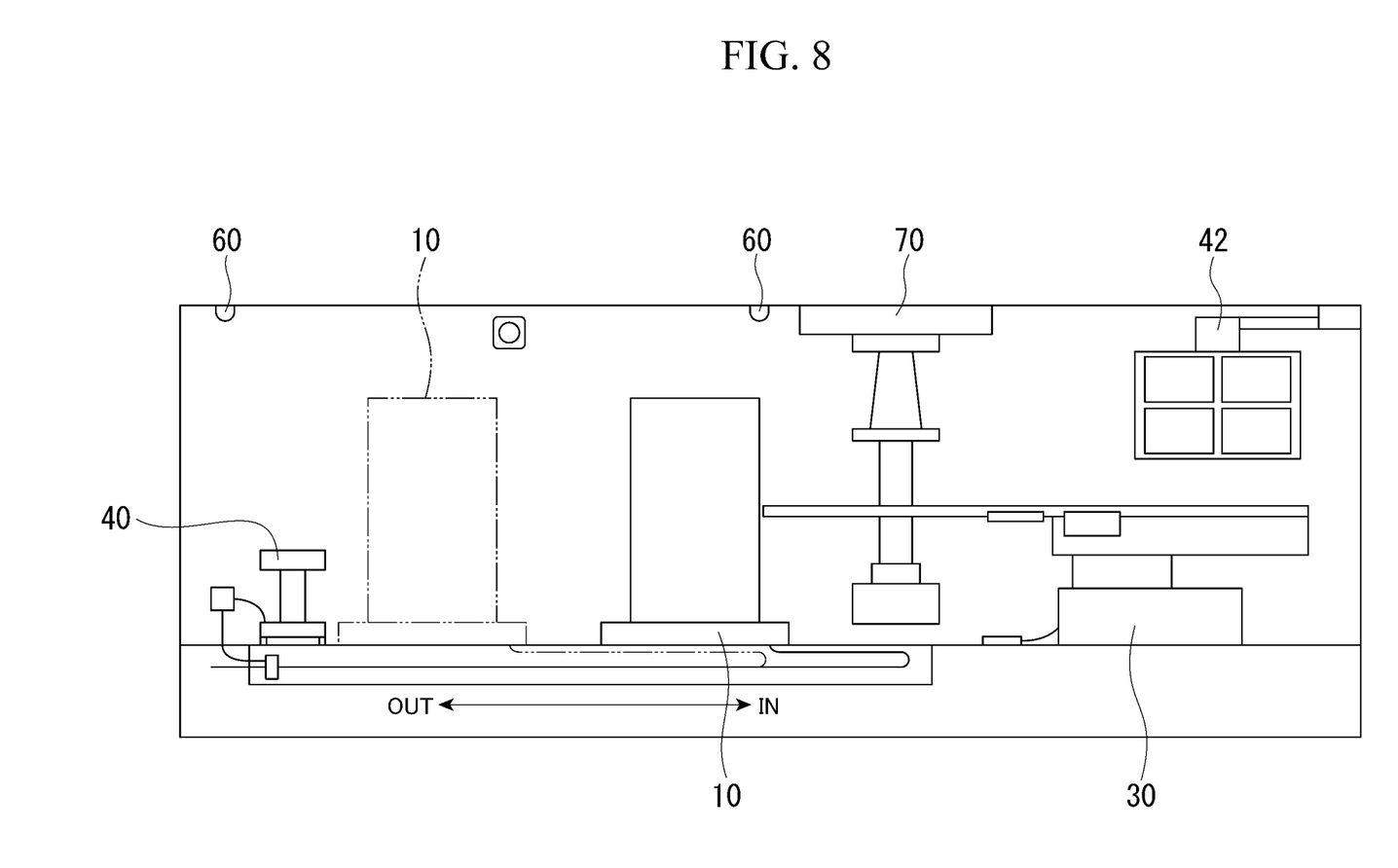
FIG. 8 is a diagram schematically showing an indoor space in which the IVR-CT apparatus 1 is installed.

FIG. 8 is a diagram schematically sowing an indoor space (hereinafter, imaging room) in which the IVR-CT apparatus 1 is installed. There are cases in which another device (hereinafter, another device C) is disposed in the imaging room in addition to the gantry 10, the bed device 30, the IVR device 70, and the display 42 of the IVR-CT apparatus 1. Imaging is performed in a state in which other medical staffs (candidates for an operator, and the like) in addition to the examination subject P and the operator have entered the imaging room.

The console device 40 may be disposed outside the imaging room or disposed outside a movable range of each device in the imaging room. In the following description of an operation prediction example, description of the console device 40 will be omitted.

Figure 9:
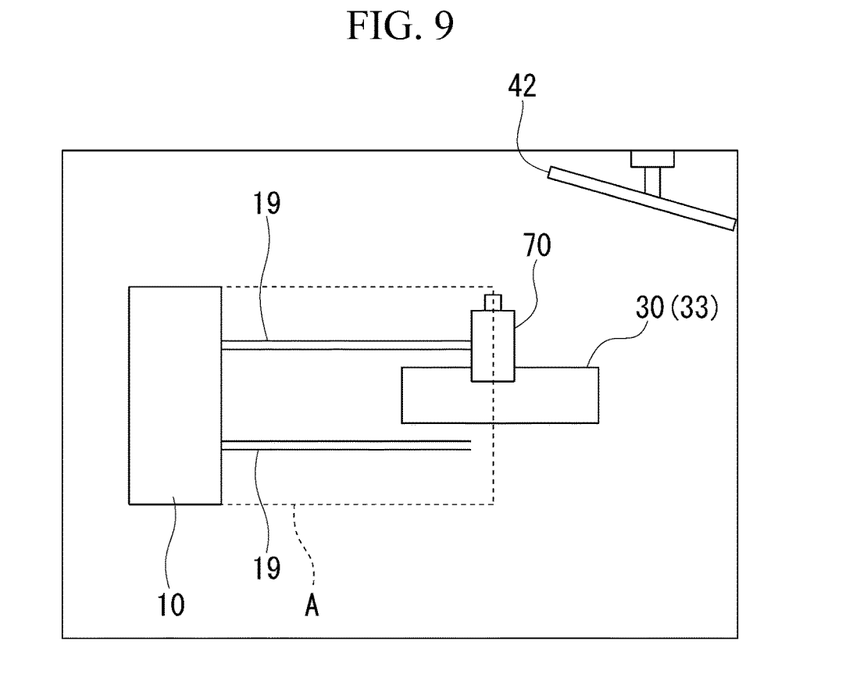
FIG. 9 is a top view showing an example of arrangement of devices of the IVR-CT apparatus 1 in an imaging room.

FIG. 9 is a top view showing an example of arrangement of devices of the IVR-CT apparatus 1 in the imaging room. In the example of FIG. 9, operation prediction targets of the operation prediction function 51 include the gantry 10, the bed device 30, the IVR device 70, and the display 42. The shown position of the gantry 10 corresponds to a home position before an operation starts.

The shown specific area A is an area of a movement range specified by the specifying function 51-2, through which the gantry 10 passes when it has moved along the moving rail 19. The specific area A may be the entire movable region from when the gantry 10 starts imaging until when the gantry 10 ends imaging or a movable region for a predetermined time (e.g., about 10 [sec]). The second acquisition function 51-3 acquires at least information for detecting whether an object that can be an interfering object is present within the specific area A specified by the specifying function 51-2.

In the example of FIG. 9, since a part of the IVR device 70 has entered the specific area A, the detection function 51-4 detects the IVR device 70 as an inference object. Although the bed device 30 has entered the specific area A like the IVR device 70, the top board 33 can be introduced into a hole part of the gantry 10 and thus the bed device may be excluded from targets as an object that cannot be an interfering object. When it is difficult to determine whether the top board 33 interferes with the gantry 10 according to images captured by the camera 60, detection of interference of the top board 33 with the gantry 10 may be performed by the sensor 62 alone.

The warning output function 51-5 outputs warning information such that the IVR device 70 is retracted. In this case, movement of the gantry 10 may be temporarily stopped.

[Operation Detection/Prediction Example 2]

The operation prediction function 51 may predict whether there is an object that can be an interfering object on the basis of a plurality of installation space images 41-5 acquired at successive timings.

In such a case, the specifying function 51-2 further specifies a timing at which the gantry 10 passes through a movement range in addition to the movement range. The detection function 51-4 predicts occurrence of an interfering object in the movement range on the basis of the timing specified by the specifying function 51-2.

Figure 10:
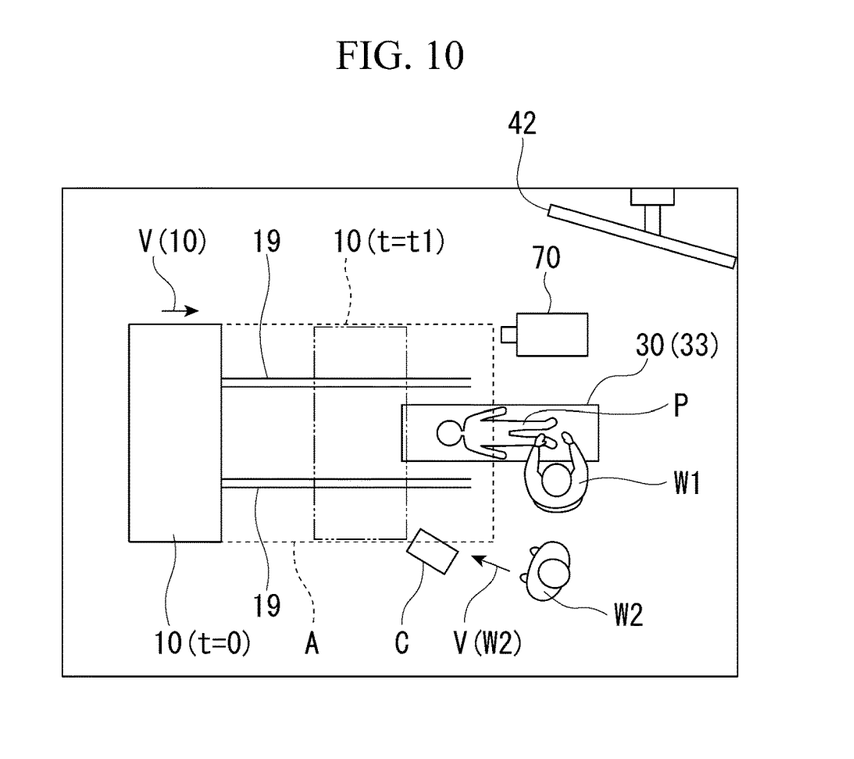
FIG. 10 is a top view showing another example of arrangement of devices of the IVR-CT apparatus 1 in the imaging room.

FIG. 10 is a top view showing another example of arrangement devices of the IVR-CT apparatus 1 in the imaging room. In the example of FIG. 10, operation prediction targets of the operation prediction function 51 include the gantry 10, the bed device 30, the TVR device 70, the display 42, the examination subject P, an operator W1, an operator W2, and the other device C. Meanwhile, "(t=0)" in the figure represents a state in which the gantry 10 is positioned at the home position (imaging start time).

The operation prediction function 51 may derive movement vectors of the other device C and persons such as operators in the imaging room on the basis of the plurality of installation space images 41-5 and predict whether each device and person can be interfering objects of the gantry 10. For example, the second acquisition function 51-3 derives a movement vector V (W2) of the operator W2 on the basis of the plurality of installation space images 41-5.

The detection function 51-4 predicts whether the operator W2 will enter the specific area A on the basis of the movement vector V (W2) derived by the second acquisition function 51-3. The detection function 51-4 detects the operator W2 as an interfering object when it is predicted that the operator W2 will enter the specific area A. In this case, the detection function 51-4 may cause the system control function 52 to stop movement of the gantry 10 or to reduce a moving speed of the gantry 10.

Although the bed device 30 and the examination subject P mounted on the top board 33 have entered the specific area A, they can be introduced into the hole part of the gantry 10 and thus may be excluded from targets as objects that cannot be interfering objects.

When the movement path prediction model 41-6 can be applied to more detailed prediction of an operation of a person, the detection function 51-4 may perform detection on the basis of operation prediction according to the movement path prediction model 41-6.

The specifying function 51-2 specifies a timing (hereinafter referred to as a timing t1) at which the side FRONT of the gantry 10 arrives at the position of the other device C on the basis of a movement vector V (10) of the gantry 10 and the movement vector V(W2) of the operator W2. Subsequently, the detection function 51-4 predicts whether the side FRONT of the gantry 10 and the other device C interfere with each other at the timing t1.

Since the other device C can be an interfering object at the timing t1 in the shown example, the detection function 51-4 predicts that interference occurs. When it is predicted that the operator W2 will move in order to take the other device C away from the specific area A (e.g., it is predicted that the operator W2 will move while stretching out his/her hand in the direction of the other device C and the operator W2 himself/herself tends to stand still from variation in the movement vector V(W2), and the like), for example, the detection function 51-4 determines that there is no interference. When it is determined that there is no interference, a timing at which the warning output function 51-5 is caused to output a warning may be delayed or a degree of warning may be reduced.

Interfering object detection processing described above may be continuously performed from the start of scanning until the gantry 10 is retracted to the home position after the end of scanning in scanogram imaging or main scan imaging.

[Processing Flow 1]

Figure 11:
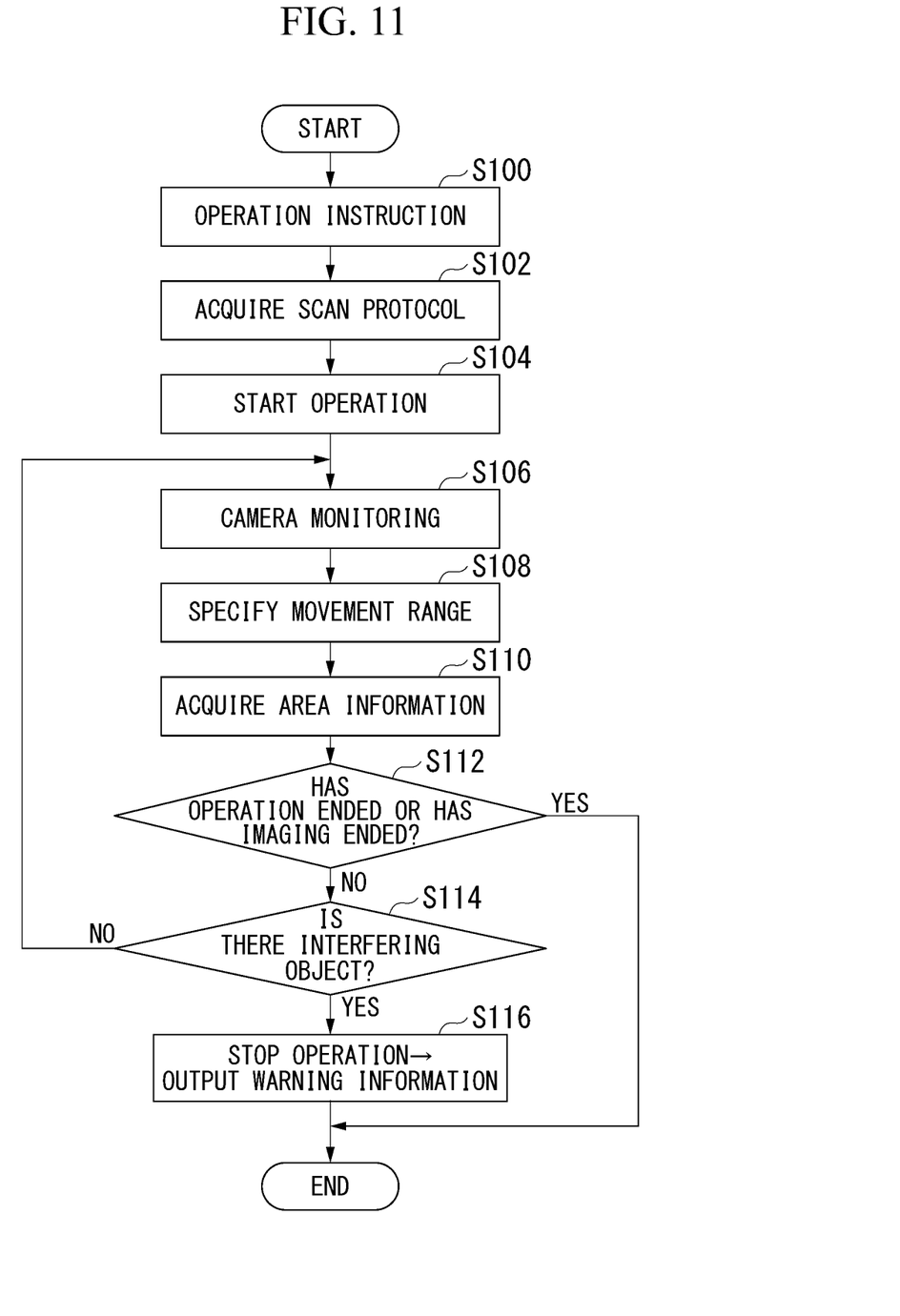
FIG. 11 is a flowchart showing an example of an imaging processing flow performed by the IVR-CT apparatus 1.

FIG. 11 is a flowchart showing an example of an imaging processing flow according to the IVR-CT apparatus 1.

First, an operator who uses the IVR-CT apparatus 1 performs an operation instruction for the IVR-CT apparatus 1 through the input interface 43 in a state in which the examination subject P is mounted on the top board 33 of the bed device 30 and setting for imaging has been performed (step S100). Subsequently, the first acquisition function 51-1 acquires information on a scan protocol from among the operation instruction received by the system control function 52 in step S100 (step S102).

Next, the system control function 52 starts the operation of the TVR-CT apparatus 1 (step S104) and starts monitoring through the camera 60 (step S106). Subsequently, the specifying function 51-2 specifies a movement range of the gantry 10 (step S108). Then, the second acquisition function 51-3 acquires information about an area including the movement range specified by the specifying function 51-2 (step S110).

Next, the system control function 52 determines whether the operation according to the operation instruction input in step S100 has ended (whether imaging has ended when the operation instruction is imaging) (step S112). When it is determined that the operation has ended, the system control function 52 ends processing of this flowchart. When it is determined that the operation has not ended, the detection function 51-4 determines whether an interfering object is detected in a specific range of the IVR-CT apparatus 1 (step S114). When an interfering object is not detected, the detection function 51-4 returns processing to step 5106. When an interfering object is detected, the detection function 51-4 causes the system control function 52 to stop the operation of the IVR-CT apparatus 1 and causes the warning output function 51-5 to output warning information (step S116). Description of processing of this flowchart ends.

[Processing Flow 2]

Figure 12:
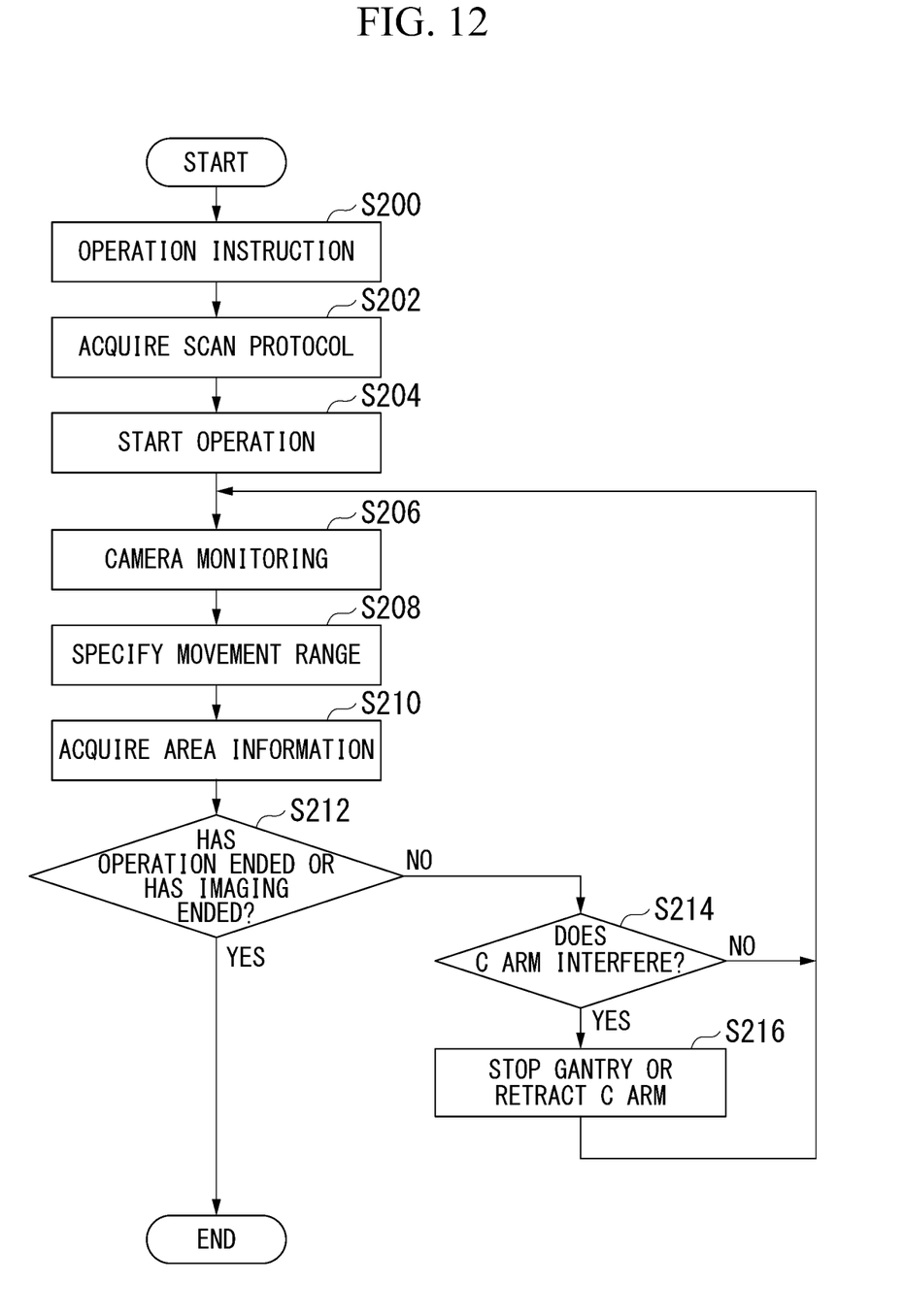
FIG. 12 is a flowchart showing an example of an imaging processing flow when an IVR device 70 is an interfering object.

FIG. 12 is a flowchart showing an example of an imaging processing flow when the gantry 10 is focused and the IVR device 70 becomes an interfering object in the IVR-CT apparatus 1.

First, an operator who uses the IVR-CT apparatus 1 performs an operation instruction for the IVR-CT apparatus 1, particularly, the gantry 10, through the input interface 43 in a state in which the examination subject P is mounted on the top board 33 of the bed device 30 and setting for imaging has been performed (step S200). Subsequently, the first acquisition function 51-1 acquires information on a scan protocol from among the operation instruction received by the system control function 52 in step S200 (step S202).

Next, the system control function 52 starts the operation of the IVR-CT apparatus 1 (step S204) and starts monitoring through the camera 60 (step S206). Subsequently, the specifying function 51-2 specifies a movement range of the gantry 10 (step S208). Then, the second acquisition function 51-3 acquires information about an area including the movement range specified by the specifying function 51-2 (step S210).

Next, the system control function 52 determines whether the operation according to the operation instruction input in step S200 has ended (whether imaging has ended when the operation instruction is imaging) (step S212). When it is determined that the operation has ended, the system control function 52 ends processing of this flowchart. When it is determined that the operation has not ended, the detection function 51-4 determines whether the IVR device 70 such that the C arm 73 is detected in a specific range (step S214). When the C arm 73 is not detected as an interfering object, the detection function 51-4 returns processing to step S206. When the C arm 73 is detected as an interfering object, the detection function 51-4 causes the system control function 52 to stop the operation of the gantry 10 or retract the C arm (step S216). The warning output function 51-5 may output warning information in step S216. Description of processing of this flowchart ends.

[Processing Flow 3]

Figure 13:
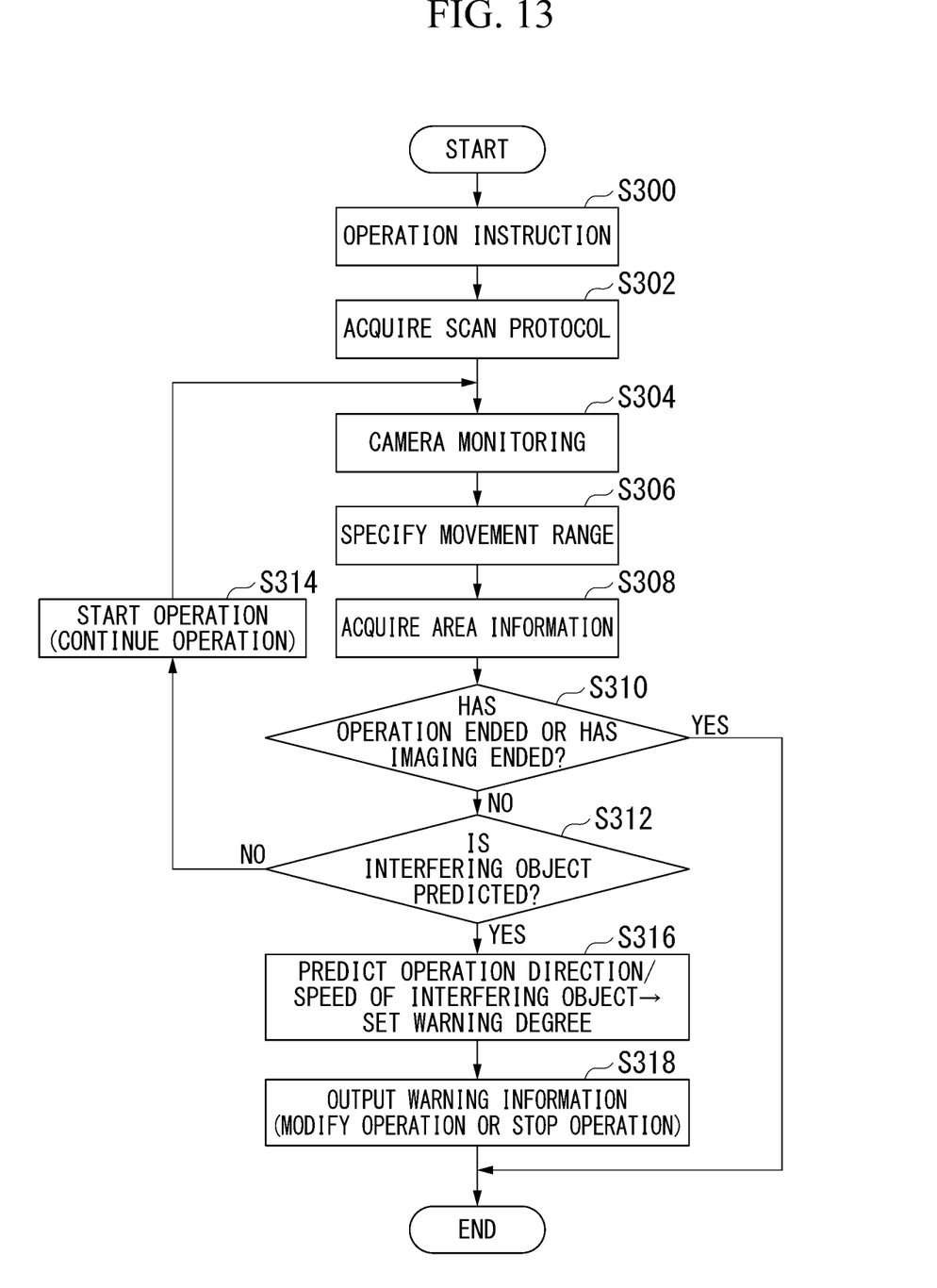
FIG. 13 is a flowchart showing another example of an imaging processing flow of the IVR-CT apparatus 1.

FIG. 13 is a flowchart showing another example of an imaging processing flow of the IVR-CT apparatus 1. Processing of the flowchart shown in FIG. 13 is an example in which a case in which an interfering object prediction capability of the detection function 51-4 is higher than that of processing of the flowchart shown in FIG. 11 is assumed. Since steps S300 to S310 shown in FIG. 13 respectively correspond to steps S100 to S110 of the flowchart shown in FIG. 11, the following description focuses on processing subsequent to step S312.

When it is not determined that the operation has ended in the process of step S310, the detection function 51-4 determines whether it is predicted that an interfering object will be detected in the specific range (step S312). When it is not predicted that an interfering object will be detected, the system control function 52 starts the operation (continues the operation when the operation has already been started) and returns processing to step S304. When it is predicted that an interfering object will be detected, the detection function 51-4 perform prediction of the operation of the IVR-CT apparatus 1 and prediction of an operation direction/operation speed of the interfering object and sets a warning degree (step S316). Subsequently, the warning output function 51-5 outputs warning information of the warning degree set in step S316 (step S318). In step S318, operation modification such as delaying the moving speed of the gantry 10 in the IVR-CT apparatus 1 or operation suspension may be performed. Description of processing of this flowchart ends.

According to at least one of the above-described embodiments, the first acquisition function 51-1 acquires a scan protocol to be executed in the gantry 10, the specifying function 51-2 specifies a movement range of the gantry 10 on the basis of the acquired scan protocol, the second acquisition function 51-3 acquires information about an area including at least the movement range of the gantry 10, and the detection function 51-4 detects or predicts presence or absence of an interfering object in the movement range specified by the specifying function 51-2 on the basis of the information acquired by the second acquisition function 51-3, and thus the gantry 10 which moves on the floor and performs scanogram imaging or main scan imaging can be prevented from coming into contact with other devices or can avoid contact.

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnostic system, comprising:
a medical image diagnostic apparatus configured to move on a floor and perform scanogram imaging or main scan imaging; and
processing circuitry configured to
acquire a scan protocol to be executed in the medical image diagnostic apparatus,
specify a movement range through which the medical image diagnostic apparatus passes when imaging a scan range included in the acquired scan protocol,
acquire a captured image of the movement range specified according to the acquired scan protocol, and
detect or predict presence or absence of an interfering object in the movement range specified according to the acquired scan protocol based on whether or not an object that can be the interfering object is present inside the movement range indicated by the image and specified according to the acquired scan protocol.

2. The medical image diagnostic system according to claim 1, wherein the acquired scan range is a scan range in scanogram imaging or a scan range in main scan imaging.

3. The medical image diagnostic system according to claim 1, wherein the processing circuitry is further configured to cause an output to output warning information when the presence of the interfering object in the movement range is detected or predicted.

4. The medical image diagnostic system according to claim 1, wherein the processing circuitry is further configured to detect or predict presence or absence of the interfering object in the movement range at the time of execution of scanning and at the time of retraction to a home position after execution of scanning.

5. The medical image diagnostic system according to claim 1, wherein the processing circuitry is further configured to
specify a timing at which the medical image diagnostic apparatus passes through the movement range in addition to the movement range, and
detect or predict presence or absence of the interfering object in the movement range based on the timing.

6. The medical image diagnostic system according to claim 1, wherein the processing circuitry is further configured to acquire space information observed in a direction perpendicular to a movement direction.

7. The medical image diagnostic system according to claim 1, wherein the main scan imaging is performed in a mode of a helical scan or a step-and-shoot scan to be executed according to movement of the medical image diagnostic apparatus.

8. The medical image diagnostic system according to claim 1, wherein the processing circuitry is further configured to
specify a timing at which the medical image diagnostic apparatus passes a first location in the movement range in addition to the movement range, and
detect or predict presence or absence of the interfering object in the movement range at the specified timing.

9. The medical image diagnostic system according to claim 1, wherein
the medical image diagnostic apparatus is a computed tomography (CT) apparatus, and
the interfering object is an Interventional Radiology (IVR) apparatus.

10. The medical image diagnostic system according to claim 1, wherein the processing circuitry is further configured to acquire, from a camera, the captured image of the area including at least the specified movement range.

11. A medical image diagnostic apparatus, comprising:
processing circuitry configured to
acquire a scan protocol,
specify a movement range through which a medical image diagnostic apparatus passed when imaging a scan range included in the acquired scan protocol, and
detect or predict presence or absence of an interfering object in the movement range specified according to the acquired scan protocol based on whether or not an object that can be the interfering object is present inside the movement range indicated by a captured image of the movement range specified according to the acquired scan protocol.

12. The medical image diagnostic apparatus according to claim 11, wherein the processing circuitry is further configured to:
specify a timing at which the medical image diagnostic apparatus passes a first location in the movement range in addition to the movement range, and
detect or predict presence or absence of the interfering object in the movement range at the specified timing.

13. The medical image diagnostic apparatus according to claim 11, wherein
the medical image diagnostic apparatus is a computed tomography (CT) apparatus, and
the interfering object is an Interventional Radiology (IVR) apparatus.

14. The medical image diagnostic apparatus according to claim 11, wherein the captured image is an image captured by a camera of the area including at least the specified movement range.

15. An IVR-CT system comprising:
a computed tomography (CT) apparatus configured to move on a floor and perform scanogram imaging or main scan imaging;
an Interventional Radiology (IVR) apparatus; and
processing circuitry configured to:
acquire a scan protocol to be executed in the CT apparatus,
specify a movement range through which the CT apparatus passes when imaging a scan range included in the scan protocol,
acquire a captured image of an area including at least the specified movement range, and
detect or predict presence or absence of the IVR apparatus in the movement range on the basis of whether or not the IVR apparatus is present inside the specified movement range indicated by the captured image.

16. The IVR-CT system according to claim 15, further comprising:
a camera, wherein the processing circuitry is further configured to acquire, from the camera, the captured image of the area including at least the specified movement range.

* * * * *